United States Patent [19]

Bosworth et al.

[11] Patent Number: 5,221,485

[45] Date of Patent: Jun. 22, 1993

[54] PURIFICATION OF X-RAY CONTRAST AGENT, MAGNETIC RESONANCE IMAGING AGENT, OR RADIOPHARMACEUTICALS USING REVERSE OSMOSIS

[75] Inventors: Mark E. Bosworth, Chesterfield; Thomas J. Dunn, Cedar Hill; Warren E. Hall, St. Louis; Richard G. Johnson, Chesterfield; Mills T. Kneller, University City; Youlin Lin, Chesterfield; Rebecca A. Wallace, Manchester; David H. White, Ballwin; David M. Wong, Chesterfield, all of Mo.

[73] Assignee: Mallinckrodt Medical, Inc., St. Louis, Mo.

[21] Appl. No.: 956,440

[22] Filed: Oct. 2, 1992

Related U.S. Application Data

[63] Continuation of Ser. No. 801,233, Dec. 3, 1991, Pat. No. 5,160,437.

[51] Int. Cl.5 .............................................. B01D 61/00
[52] U.S. Cl. ...................................... 210/651; 210/652; 210/653; 210/654; 210/00.38; 210/490; 210/644; 210/650; 424/1.1; 424/9; 424/5; 514/8; 564/153
[58] Field of Search ............... 210/651, 652, 653, 654, 210/500.38, 490, 644, 650; 424/1.1, 15, 9, 5; 514/8; 564/153

[56] References Cited

U.S. PATENT DOCUMENTS

| | | | |
|---|---|---|---|
| 4,277,344 | 7/1981 | Cadotte | 210/654 |
| 4,385,046 | 5/1983 | Milbrath et al. | 424/1.1 |
| 5,019,371 | 5/1991 | Lin et al. | 424/5 |
| 5,160,437 | 11/1992 | Bosworth et al. | 210/651 |

Primary Examiner—Robert A. Dawson
Assistant Examiner—Ana M. Fortuna
Attorney, Agent, or Firm—Rita D. Vacca

[57] ABSTRACT

The use of reverse osmosis as an alternative or substitute method for the purification of a crude diagnostic agent. X-ray contrast agent, magnetic resonance imaging agent, or radiopharmaceuticals are purified by passing through a cross-linked reverse osmosis membrane.

3 Claims, 1 Drawing Sheet

PURIFICATION OF X-RAY CONTRAST AGENT, MAGNETIC RESONANCE IMAGING AGENT, OR RADIOPHARMACEUTICALS USING REVERSE OSMOSIS

This is a continuation of application Ser. No. 07/801,233 filed Dec. 3, 1991 and now U.S. Pat. No. 5,160,437.

FIELD OF THE INVENTION

The present invention relates to the use of reverse osmosis as an alternate or substitute method for the purification of a crude diagnostic agent, and more particularly, to an improved method of purifying crude Ioversol by removing a variety of small molecular weight process impurities present in the crude form thereof.

BACKGROUND OF THE INVENTION

Ioversol is disclosed as a useful nonionic X-ray contrast agent in U.S. Pat. No. 4,396,598 incorporated herein by reference. N,N'-bis(2,3-dihydroxypropyl)-5-[N(2-hydroxyethyl) glycolamido] -2,4,6-triiodoisophthalamide, more commonly called Ioversol has the following structure:

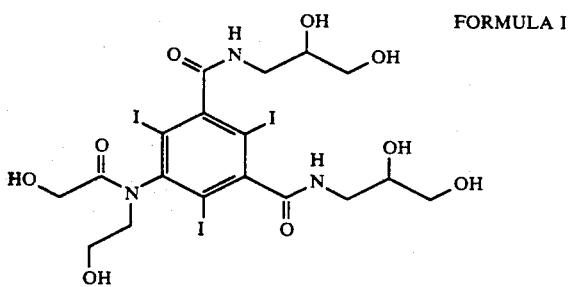

FORMULA I

In the production of Ioversol, purification columns are used to remove impurities from the crude Ioversol product following completion of the synthetic steps as described in U.S. Pat. No. 4,396,598 and incorporated herein by reference. The costs and time involved in a purification operation, such as regenerating and replacing the purification columns is significant in the purification of Ioversol. Large amounts of costly resins and large volumes of solutions are also necessary to regenerate the purification columns between uses. These costs are significant in the production of Ioversol.

An improved procedure which eliminates the need for costly purification columns to remove low molecular weight impurities from the crude Ioversol product following synthesis thereof is desired as an alternative and/or a more cost efficient method of producing Ioversol. It is, therefore, an object of the present invention to meet these needs.

Additional objects and features of the present invention will appear from the following description in which the preferred methods are set forth in detail in conjunction with the accompanying drawings.

FIG. 1 is a schematic cross-sectional view of a reverse osmosis system.

SUMMARY OF THE INVENTION

The present invention is a method of purifying crude Ioversol, without the costly use of purification columns, by using reverse osmosis to remove a variety of low molecular weight impurities therefrom. Reverse osmosis works by passing the crude Ioversol through a pressurized cartridge containing a polyamide membrane bonded to a support membrane. Low molecular weight impurities present in the crude Ioversol and some water pass through the pores of the polyamide membrane to comprise the permeate stream. The then purified Ioversol having a higher molecular weight does not pass through the polyamide membrane pores but rather exits from the cartridge to return to the process tank. This improved process greatly reduces the amount of product customarily loss through absorption by the resin portion of chromatography purification column and significantly reduces operating costs since no resin regeneration is required. Additionally, no waste streams are produced as with the regeneration of chromatography purification columns. Reverse osmosis can also be extended beyond currently known uses and used to remove a variety of low molecular weight organic and inorganic and iodinated impurities from a nonionic radio-opaque process streams such as in the production of Ioversol. Impurities which may be removed from the crude Ioversol by reverse osmosis include ethyleneglycol having a molecular weight of 62, dimethylsulfoxide having a molecular weight of 78 and formaldehyde having a molecular weight of 30 as opposed to Ioversol having a molecular weight of 807. Reverse osmosis may also be used in the purification of magnetic resonance imaging agents and radiopharmaceuticals.

An alternative method of purification for crude process streams such as those just described is greatly needed to reduce the cost of producing such agents. Reverse osmosis fulfills that need by reducing the amount of product lost during purification and reducing operational costs through the elimination of the need for resin regeneration.

DETAILED DESCRIPTION OF THE INVENTION

Figure 1:
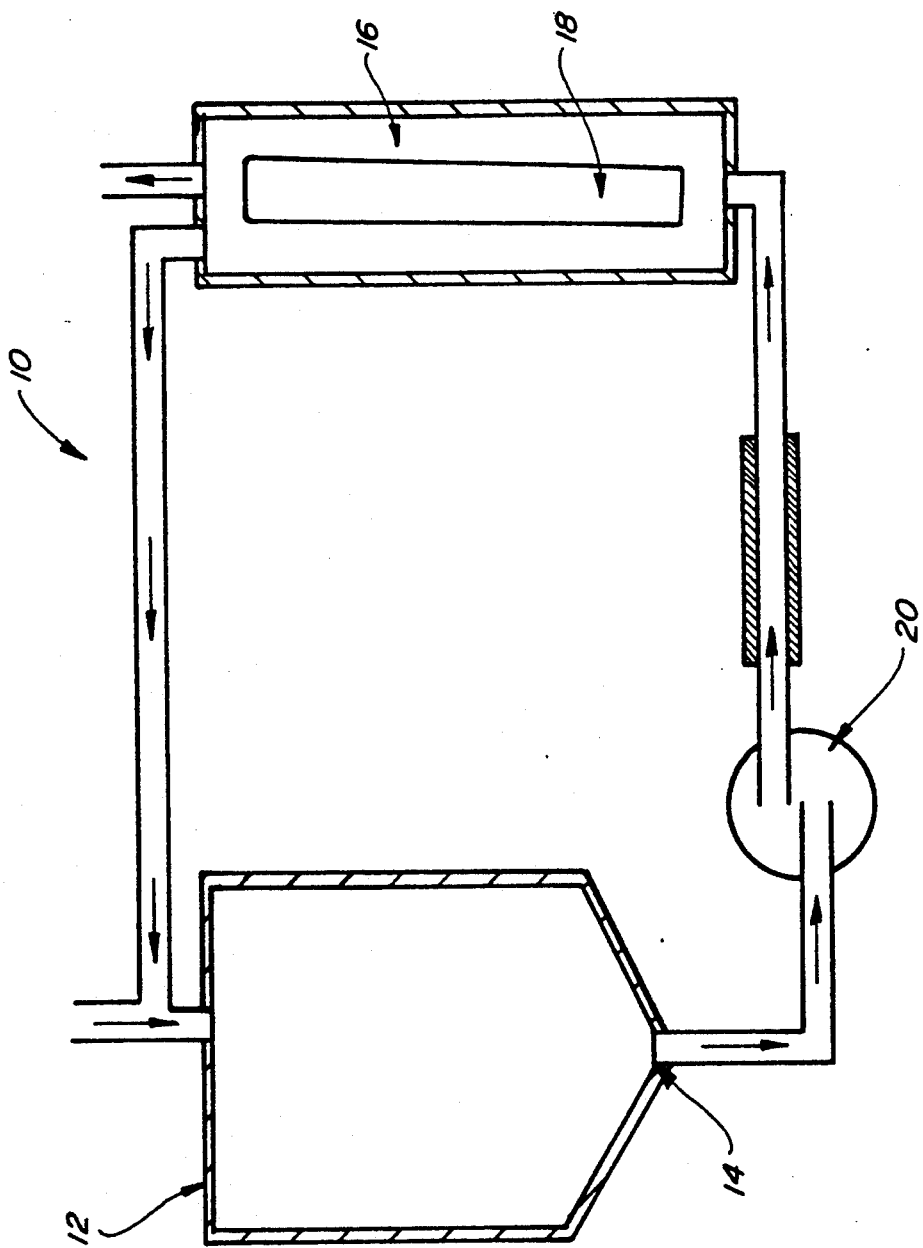

Crude Ioversol once produced must be purified prior to its use as a x-ray contrast agent. Currently, chromatography purification columns are used for this purpose. However, reverse osmosis may be used as a separation technology to remove low molecular impurities from the crude Ioversol through the use of housing cartridges containing specially designed polyamide membranes. Reverse osmosis has the removal efficiency of chromatography purification columns without the need for chemical regeneration between cycles. This means reverse osmosis can purify product streams while lowering overall operating costs by eliminating the costly regeneration of chemicals. Reverse osmosis removes small molecular weight impurities, such as but not limited to ethylene glycol, propylene glycol, dimethylsulfoxide, chlorinated $C_{1-10}$ alkyls, $C_{1-10}$ alcohols and formaldehyde from crude Ioversol with use of the reverse osmosis system illustrated in FIG. 1.

The reverse osmosis system 10 illustrated in FIG. 1 is known to those skilled in the art for use in removing salt ions from water and removing alcohol from fermented beverages. Reverse osmosis system 10 is also capable of removing a variety of impurities from the crude Ioversol process stream without the need for chemical regeneration cycles which is the subject of the present invention. The crude Ioversol stream is drawn into process tank 12 which is half filled with the crude Ioversol and continuously maintained at that level. The crude Ioversol then drains through the bottom 14 of process tank 12, allowing the crude Ioversol to pass into pump 20 which pumps the crude Ioversol into housing cartridge 16. Housing cartridge 16 contains layered specially designed polyamide or similar such membrane(s) 18 which allow passage of an aqueous solution of the low molecular weight impurities to a waste stream while allowing the larger molecular weight Ioversol to pass through the housing cartridge 16 unabsorbed and return to the process tank 12. This procedure may be repeated one or more times depending on the level of purification desired. During this improved purification process, pump 20 creates the pressure which is in the range of 100 to 1,200 pounds per square inch or 7 to 80 atmospheres within housing cartridge 16 to force low molecular weight impurities in an aqueous solution to pass through the specially designed membrane to form a permeate stream while the Ioversol passes over the membrane without being absorbed to return to process tank 12 to form a retentate stream.

The polyamide membrane 18 described in more detail is a cross-linked polymer matrix synthesized directly from an essentially monomeric polyacyl halide and an essentially monomeric arylene polyamine with a measurable water solubility, as described in U.S. Pat. No. 4,277,344 incorporated herein by reference. The present invention for the improved method of removing impurities from nonionic x-ray contrast agents such as Ioversol radiopharmaceuticals or magnetic resonance imaging agents through the reverse osmosis process is further illustrated by the following examples, but is not intended to be limited thereby.

EXAMPLE 1

Procedure for Removal of Small Molecular Weight Impurities from Ioversol by Reverse Osmosis This reverse osmosis purification procedure was developed and tested using a Millipore Prolab ™ (manufactured by Millipore Corporation, Bedford, Mass. 01730) laboratory reverse osmosis unit. However, similar such machines available in the market would work as well. The procedure could have also been scaled up to accommodate larger reverse osmosis units.

The housing cartridge portion of the Millipore Prolab unit described in this example contained a membrane having 3 feet of surface area having a 400 molecular weight cut off. This particular cartridge is designated a Model R75A by the Millipore Corporation. The working component of the membrane was a thin polyamide sheet bonded to a polysulfone support.

A. The Reverse Osmosis Unit and Cartridge Preparation For A Dry R7SA Cartridge

(1) Washing

The housing cartridge was immersed in deionized depyrogenated water for 16 hours. The water was allowed to continuously overflow to remove any manufacturing residues present on the housing cartridge. Samples were taken at the beginning and at the end of the overflow and tested for manufacturing residues. The cartridge was then installed in the cartridge holder. The housing cartridge was washed with deionized-depryogenated water at 225 pounds per square inch of inlet pressure controlled by the back pressure control valve for 10 minutes with both the retentate and the permeate streams directed to the drain. Then the retentate line was directed to the process feed tank while the permeate line remained directed to the drain. The housing cartridge was then washed at a pressure of 225 pounds per square inch for one hour at a temperature of 25°-40° C. with depyrogenated-deionized water. Samples were taken after 10, 30, and 60 minutes and tested for manufacturing residues. Residues should not be detectable after 10 minutes.

(2) Standard Water Flux

The retentate and the permeate lines were both directed to the feed tank and the water was recycled for 10 minutes at 200 pounds per square inch inlet pressure at a temperature of 25° C. The water was maintained at a cool temperature on the jacket of the Millipore Prolab unit to maintain a temperature of 25° C. inside. The standard water flux was determined at 200 pounds per square inch inlet pressure by collecting water from the permeate line. The flow was determined with a stopwatch and a graduated cylinder. The flow was then converted to flux in liters per meter$^2$ per hour by using the conversion formula:

$$\text{liters/m}^2/\text{hour} = \frac{\text{ml/min}}{\text{membrane area in ft}^2} \times .65$$

(3) Integrity Test

This test was used to determine if the cartridge had been properly installed and to insure that no manufacturing defects existed. First, the Prolab unit was completely drained. Two liters of 2011 ppm MgSO$_4$ solution were prepared and placed in the feed tank. The permeate and the retentate lines were then directed to the feed tanks for full recycle. Recycling was conducted with the pump set at six liters per minute and the inlet pressure set at 225 pounds per square inch at a temperature of 25° C. for 20 minutes. The pressure was then fully stabilized. Samples of the retentate were collected from the feed tanks and samples of the permeate were collected from the feed line. The MgSO$_4$ concentration was then determined by conductivity and the percentage of rejections was determined using the following formula:

*Percent rejection for* MgSO$_4$=[1-*(concentration of permeate/concentration of feed)*]×100.

An R7SA cartridge should have a percentage rejection greater than 95%. The MgSO$_4$ solution was then drained and the Prolab unit was rinsed with deionized water for 50 minutes with both the retentate and the permeate lines directed to the drain. A sample was collected from each line and tested for MgSO$_4$. Less than 5 ppm MgSO$_4$ should be present.

(4) Final Cartridge Cleaning

The cartridge holder was filled with deionized water and the cartridge was soaked in the deionized water for 16 hours. A sample of the water from within the housing cartridge was then tested for manufacturing residues. Residues were and should be nondetectable. Two liters of deionized water were placed in the feed tank and the water was recycled through both the retentate and the permeate lines for approximately four minutes at a pressure of 50 pounds per square inch. Then, this water was tested for manufacturing residues. Residues once again were and should be nondetectable. Two liters of deionized water were placed in the feed tank and the water recycled through both the retentate and the permeate lines for four minutes at a pressure of 50 pounds per square inch. Again, this water was tested for manufacturing residues. Residues were and should be nondetectable.

(5) Sanitizing the Cartridge

All water was drained from the interior of the Millipore Prolab unit. Two liters of 0.01N NaOH were prepared and placed in the feed tank. This solution was then recycled through the reverse osmosis unit for 30 minutes at 200 pounds per square inch inlet pressure. The temperature was maintained at 40° to 45° C. to kill any bacteria present. However, a temperature of 45° C. was not exceeded because 45° C. was the working limit of the cartridge. The solution was drained from the housing cartridge, and all residual NaOH was rinsed out with depyrogenated water.

(6) Standard Water Flux

The standard water flux was determined at 200, 300, 400 pounds per square inch inlet pressure. These flux values were later used to determine the cartridge performance.

B. Diafiltration to Remove Ethylene Glycol from Ioversol

The cartridge and reverse osmosis unit were prepared as described in Section A above.

(1) Equilibration of Feed Solution

An Ioversol solution was prepared with deionized water and the ethylene glycol content of the solution was determined. The Ioversol concentration was and should be within the range of 1 to 40 percent weight per volume. The solution was then placed in the feed tank. Both the retentate and the permeate lines were directed to the feed tanks for total recycle. Recycling was continued for 30 minutes at a pressure of 200 pounds per square inch at six liters per minute and at a temperature of 25° C. The flux was stabilized. During this period an Ioversol layer formed on the membrane. The inlet pressure was adjusted to the desired operating pressure within the 200 to 500 pounds per square inch range. Preferably, a pressure of 400 pounds per square inch should be used for 24 percent weight per volume Ioversol solutions. Recycling was continued for 30 minutes to obtain a stable pressure and flux.

(2) Operation

The permeate line was then redirected to collection flasks while simultaneously introducing deionized water into the feed tank. The incoming water flow was adjusted to match the outgoing flow of permeate. The reverse osmosis unit remained in a continuous diafiltration mode when operated as so described. Diafiltration defined as the removal of a permeable solute during reverse osmosis by adding fresh solvent to the feed tank was achieved. During diafiltration the solvent that was pumped into the feed tank was called a "wash". When the volume of the wash equaled the feed volume, one wash was complete. The solid Ioversol feed used to prepare the feed solution contained about 300 ppm ethylene glycol (EG) and four to six washes were required to obtain Ioversol that contained 2 to 50 ppm ethylene glycol. Most commonly, the feed solution was washed until the desired level of ethylene glycol was reached as determined by high performance liquid chromatography or gas chromatography methods. More washes were also needed if higher levels of ethylene glycol were present in the feed. For example, an 11.3% weight per volume solution of Ioversol was prepared from solid Ioversol that contained 1690 ppm ethylene glycol. After six washes at a pressure of 300 pounds per square inch and a temperature of 25° C., the ethylene glycol content was about 11 ppm. After seven washes, the ethylene glycol content was nondetectable. When washing was completed, the addition of water to the feed tanks was stopped. If the feed was relatively dilute, for example 12% weight per volume, diafiltration was continued to obtain about a 24% weight per volume solution. The 24% solution was drained out into a collection flask. Deionized water was placed in the feed tank and the water was recycled through the reverse osmosis unit for 5 minutes at a pressure of 200 pounds per square inch. The rinse solution was combined with the feed solution. Rinsing was repeated until all the Ioversol was recovered.

C. Diafiltration to Remove Dimethylsulfoxide and Ethylene Glycol from Ioversol The continuous diafiltration was conducted as described above. Washing was continued until the desired level of ethylene glycol and dimethylsulfoxide (DMSO) were achieved. For example, 257 grams of Ioversol which contained 881 ppm DMSO and 531 ppm ethylene glycol was diluted to obtain a 12.85% weight per volume solution. The Ioversol solution was diafiltered at a pressure of 300 pounds per square inch inlet pressure. DMSO was not detectable after eight washes.

D. Diafiltration to Remove Trichloroethane, Amyl Alcohol, DMSO and Formaldehyde from Ioversol Solutions First, a 2755 ml of an 11.88% weight per volume solution of Ioversol was prepared. 1,1,2-trichloroethane was added to a concentration of 19.5 micrograms per milliliter. Amyl alcohol was added to a concentration of 19.5 micrograms per milliliter. DMSO was added to a concentration of 46.5 micrograms per milliliter and formaldehyde was added to a concentration of 4.89 micrograms per milliliter. A R-55A housing cartridge was used in this process. This particular cartridge also has a 400 molecular weight cutoff continuous diafiltration was conducted at a pressure of 200 pounds per square inch and a temperature of 25° C. as described above. After five washes, the feed solution was assayed again for the four components that had been added, 1,1,2-trichloroethane, amyl alcohol and dimethylsulfoxide were not detectable. The formaldehyde concentration was 0.58 micrograms per milliliter. The R25A membrane has a 100 molecular weight cutoff and permits the slowest flux of Ioversol through its membrane. However, loss of Ioversol in the permeate with the R25A cartridge is much less than the loss experienced with the R75A and R55A membranes. If any of the impurities listed above are present in the crude Ioversol solution, each may be removed by diafiltration of the crude Ioversol solution through either a R75A, R55A or R25A cartridge. These cartridges primarily differ in effectiveness only by the number of washes needed to accomplish the removal of the impurity and the quantity of Ioversol lost in the permeate.

E. Diafiltration to Remove Propylene Glycol, Methanol Dichloromethane, Chloroform and Ethanol from Ioversol Solutions Continuous diafiltration is conducted as described above to remove any of these and other $C_{1-10}$ alcohols and chlorinated $C_{1-10}$ alkyls from Ioversol solutions.

F. Diafiltration to Remove Ethylene Glycol, DMSO, Formaldehyde, 1,1,2-Trichloroethane, Amyl Alcohol, Ethanol, Methanol and Propylene Glycol Using R75A, R55A or R25A Model Cartridges The R75A cartridge contains a 400 molecular weight cutoff membrane and permits slow flux of Ioversol solutions through the membrane during continuous diafiltration. The R55A cartridge also contains a 400 molecular weight cutoff membrane and permits a faster flux of Ioversol solutions through the membrane during continuous diafiltration. The R25A cartridge contains 100 molecular weight cutoff membrane and permits a very slow flux of Ioversol solutions through the membrane during continuous diafiltration but results in significantly less loss of Ioversol during the purification process.

The improved method of purification for nonionic x-ray contrasts and similar such diagnostic agents of the present invention as exemplified above, is less expensive, easier to perform and results in significantly fewer impurities than currently used purification processes.

Accordingly, having described the invention,

We claim:

1. A method for the purification of a crude x-ray contrast agent, magnetic resonance imaging agent or radiopharmaceutical comprising the steps of:
   a) passing a crude agent into a housing cartridge containing a cross-linked membrane; and
   b) applying pressure within said housing cartridge to force said crude agent into said cross-linked membrane whereby low molecular weight impurities within said crude agent are forced through pores in said cross-linked membrane and purified agent passes over said cross-linked membrane.

2. A method of purification according to claim 1 wherein said pressure within said housing cartridge is within the range of 100 to 1200 pounds per square inch or 7 to 80 atmospheres.

3. The process of purification according to claim 1 wherein said low molecular weight impurities are selected from the group consisting of ethylene glycol, propylene glycol, dimethylsulfoxide, chlorinated $C_{1-10}$ alkyls, $C_{1-10}$ alcohols and formaldehyde.

* * * * *